(12) United States Patent
Lee et al.

(10) Patent No.: US 7,468,456 B2
(45) Date of Patent: Dec. 23, 2008

(54) AZEOTROPIC DISTILLATION PROCESS FOR SEPARATING ACETIC ACID, METHYLACETATE AND WATER IN THE PRODUCTION OF AN AROMATIC CARBOXYLIC ACID

(75) Inventors: Myron Myonkee Lee, Seongnam-si (KR); Duk-Jun Kwon, Seoul (KR); Dong-Won Lee, Anyang-si (KR); Alexander Jongwon Lee, Seongnam-si (KR)

(73) Assignee: ANT Corporation, Gyeonggi-do (KR)

( * ) Notice: Subject to any disclaimer, the term of this patent is extended or adjusted under 35 U.S.C. 154(b) by 239 days.

(21) Appl. No.: 11/484,801

(22) Filed: Jul. 11, 2006

(65) Prior Publication Data

US 2007/0027340 A1 Feb. 1, 2007

(30) Foreign Application Priority Data

Aug. 1, 2005 (KR) ...................... 10-2005-0070358

(51) Int. Cl.
*C07C 51/16* (2006.01)
*C07C 51/265* (2006.01)

(52) U.S. Cl. ...................................... 562/409; 562/414

(58) Field of Classification Search ................. 562/409, 562/414
See application file for complete search history.

(56) References Cited

U.S. PATENT DOCUMENTS

| | | | | | |
|---|---|---|---|---|---|
| 2,893,923 | A | * | 7/1959 | Luke, Jr. et al. | 203/31 |
| 3,392,091 | A | * | 7/1968 | Hohenschutz | 203/71 |
| 4,250,330 | A | | 2/1981 | Costantini et al. | 562/409 |
| 4,329,493 | A | * | 5/1982 | Hashizume et al. | 562/414 |
| 5,510,521 | A | * | 4/1996 | McGehee et al. | 562/414 |
| 5,980,696 | A | * | 11/1999 | Parten et al. | 203/1 |
| 6,143,926 | A | | 11/2000 | Parten | 562/414 |
| 6,150,553 | A | * | 11/2000 | Parten | 560/248 |
| 7,048,835 | B2 | * | 5/2006 | Jang et al. | 203/16 |
| 2006/0235242 | A1 | * | 10/2006 | Kang | 562/410 |

FOREIGN PATENT DOCUMENTS

| | | | | |
|---|---|---|---|---|
| JP | 2005247835 A | * | 9/2005 | |
| JP | 2007063153 A | * | 3/2007 | |
| WO | WO9729068 A1 | * | 8/1997 | |
| WO | WO 9845239 A1 | * | 10/1998 | |
| WO | WO 2005075404 A1 | * | 8/2005 | |

* cited by examiner

*Primary Examiner*—Daniel M Sullivan
*Assistant Examiner*—Louisa Lao
(74) *Attorney, Agent, or Firm*—Occhiuti Rohlicek & Tsao LLP

(57) ABSTRACT

An improved process for producing an aromatic carboxylic acid from an aromatic alkyl hydrocarbon is described, wherein the improvement comprises using the same aromatic alkyl hydrocarbon as the azeotropic agent for separation of acetic acid and methyl acetate from water via azeotropic distillation. The process of this invention has considerable advantages over other known processes, particularly in regards to consumption of the azeotropic agent and utilities, formation of undesirable impurities and operating costs.

7 Claims, 1 Drawing Sheet

AZEOTROPIC DISTILLATION PROCESS FOR SEPARATING ACETIC ACID, METHYLACETATE AND WATER IN THE PRODUCTION OF AN AROMATIC CARBOXYLIC ACID

This application claims the benefit of the filing date of Korean Patent Application No. 10-2005-0070358, filed on Aug. 1, 2005 in the Korean Intellectual Property Office, the disclosure of which is incorporated herein in its entirety by reference.

BACKGROUND OF THE INVENTION

1. Field of the Invention

This invention relates to an improved process for separating acetic acid and methyl acetate from water using certain organic compounds as the azeotropic agent in azeotropic distillation. Specifically, in a process for manufacturing an aromatic carboxylic acid by oxidizing an aromatic alkyl hydrocarbon, this invention is concerned with a method of azeotropic distillation using the said aromatic alkyl hydrocarbon as the azeotropic agent for the separation of acetic acid and methyl acetate from water.

2. Description of the Related Art

Water and methyl acetate are produced as by-products in the process of manufacturing an aromatic carboxylic acid, such as terephthalic acid and isophthalic acid, wherein an aromatic alkyl hydrocarbon such as p-xylene and m-xylene, respectively, is oxidized with air in the presence of an acetic acid solvent and a catalyst system comprised of cobalt, manganese and bromine. A portion of the condensed liquid from the vapor stream of the oxidation reactor and other dilute acetic acid streams, containing mostly water and methyl acetate, are sent to the dehydration unit to recover concentrated acetic acid and to remove the oxidation by-products, which are mainly water and methyl acetate.

In the above-described method of the prior art for the commercial production of aromatic carboxylic acids, the conventional distillation method is widely used in the dehydration unit to recover concentrated acetic acid and to remove water and methyl acetate from the system. The recovered acetic acid is recycled back to the oxidation reactor for reuse as the solvent, while water and methyl acetate are sent to the wastewater treatment system. This method has several drawbacks such as low recovery rate of acetic acid, excessive steam consumption, total loss of methyl acetate, and very high wastewater treatment costs due to the high concentration of acetic acid and methyl acetate in wastewater. Furthermore, unreacted aromatic alkyl hydrocarbons present in the feed stream to the dehydration unit are lost to wastewater, resulting in a lower yield of aromatic carboxylic acid.

U.S. Pat. No. 4,250,330 describes an azeotropic distillation process for the dehydration unit to separate acetic acid and methyl acetate from water, in which isobutyl acetate is used as the azeotropic agent. In this process, methyl acetate is recovered from the top of the stripping column and then the recovered methyl acetate is recycled to the oxidation reactor of p-xylene. Despite some improvements over the conventional distillation method such as lower steam consumption and recovery of methyl acetate, this process has the following drawbacks:

(a) A small amount of isobutyl acetate contained in the streams of recovered acetic acid and methyl acetate is recycled back to the p-xylene oxidation reactor and is then decomposed to isobutanol, propanol, methanol, and carbon oxides (CO and CO2). Therefore, the consumption rate of isobutyl acetate is high. The decomposition products, isobutanol, propanol and methanol, further react with organic radicals in the oxidation reactor, producing a number of impurities, which contaminate the process streams and the terephthalic acid product. Unreacted isobutanol, propanol and methanol are then introduced into the dehydration unit along with the dilute acetic acid streams. These alcohol compounds significantly affect the performance of the dehydration unit, causing poor separation and higher consumption of steam and cooling water.

(b) Small amounts of p-xylene and isobutanol contained in the feed to the dehydration unit build up to high concentrations in the organic phase because removal of these chemicals from the dehydration unit is very difficult. Large amounts of p-xylene and isobutanol circulating in the dehydration unit increase consumption of steam and cooling water and lower the separation efficiency.

U.S. Pat. No. 5,980,696 describes a method of using isobutyl acetate or n-propyl acetate as the azeotropic agent to separate water from acetic acid by azeotropic distillation, but this process also has similar drawbacks to those mentioned above for U.S. Pat. No. 4,250,330.

BRIEF SUMMARY OF THE INVENTION

An object of the present invention is therefore to provide an improved process for separating acetic acid and methyl acetate from water using specific organic compounds as the azeotropic agent in azeotropic distillation. Another object of the present invention is to eliminate the drawbacks of the prior art processes mentioned herein above. Other objects of this invention will be apparent from the following description.

In a process for producing an aromatic carboxylic acid by oxidizing an aromatic alkyl hydrocarbon, the present invention provides an improved process of azeotropic distillation, using the said aromatic alkyl hydrocarbon as the azeotropic agent for the separation of acetic acid and methyl acetate from water.

In the manufacturing process of an aromatic carboxylic acid in which an aromatic alkyl hydrocarbon is oxidized with an oxygen-containing gas in acetic acid solution, at a temperature within the range of 150 to 220° C. and at a pressure within the range of 10 to 25 kg/cm (abs.), and in the presence of a catalyst system containing cobalt, manganese and bromine, whereby water and methyl acetate are produced as by-products of oxidation, and a portion of the condensed liquid from the overhead vapor stream of the oxidation reactor and other dilute acetic acid streams, containing mostly water and methyl acetate, are sent to the dehydration unit (the composite feed of all dilute acetic acid streams to the dehydration unit is hereinafter referred to as the "feed stream") where water and methyl acetate are separated from acetic acid, the improvement in the recovery of the acetic acid and the methyl acetate comprises the following steps:

(a) feeding said feed stream to an azeotropic distillation column in which the azeotropic agent is the same aromatic alkyl hydrocarbon as the feedstock used for the production of the aromatic carboxylic acid; for example, the azeotropic agent is p-xylene for terephthalic acid, m-xylene for isophthalic acid and pseudocumene for trimellitic acid;

(b) withdrawing concentrated acetic acid from the bottom of said azeotropic distillation column, condensing the vapor stream of said azeotropic distillation column which is comprised of azeotropic agent, water and methyl acetate, feeding the liquid condensate to a decanter, separating said condensate into an aqueous phase and an organic phase, refluxing a small portion of the aqueous-phase liquid and a major portion of the organic-phase liquid to the top region of said azeotropic distillation column, withdrawing a major portion of the aqueous-phase liquid comprised predominantly of water and methyl acetate, withdrawing a small portion of the organic-phase liquid comprised predominantly of azeotropic agent and small amounts of methyl acetate and water;

(c) recycling said concentrated acetic acid and withdrawn organic-phase liquid to the oxidation zone of the aromatic alkyl hydrocarbon, and supplying the withdrawn aqueous-phase liquid to a distillation column in which water and methyl acetate are separated from the bottom and the top of said distillation column, respectively.

DETAILED DESCRIPTION OF THE INVENTION

Figure 1:
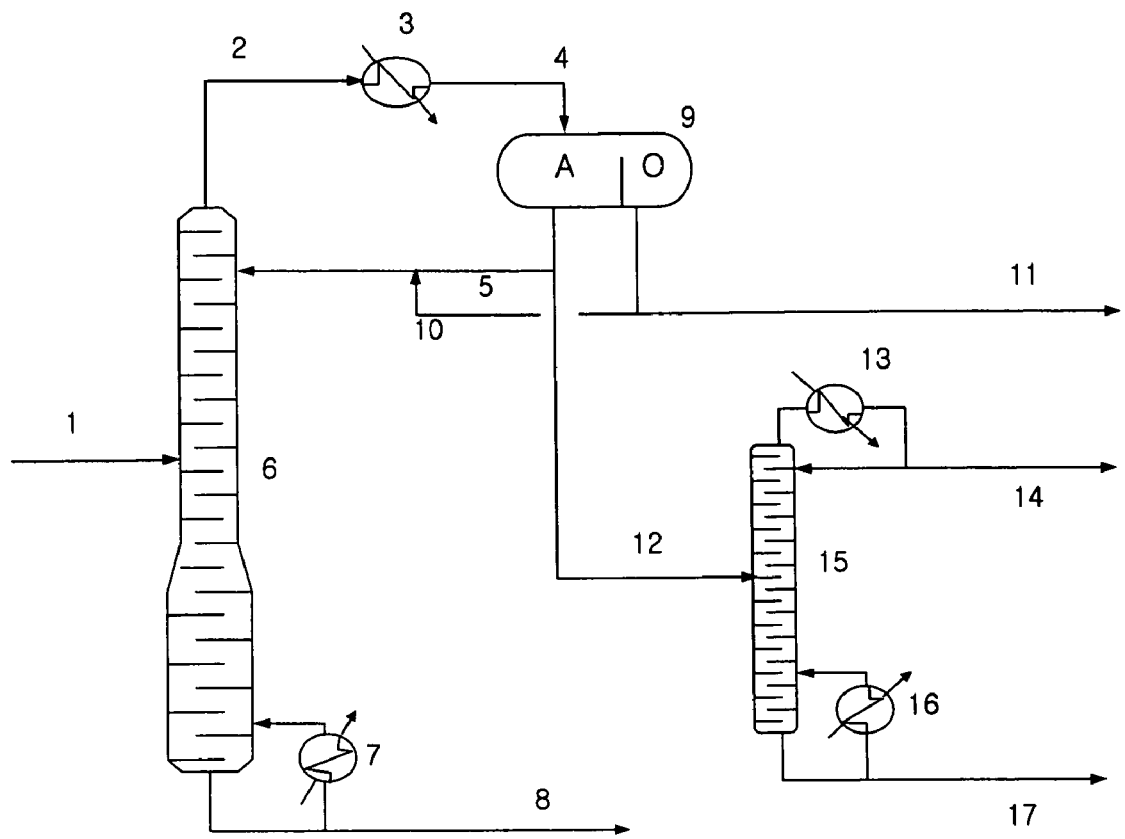
FIG. 1 is a flow diagram, showing the general configuration of this invention.

In a process of manufacturing an aromatic carboxylic acid by oxidizing an aromatic alkyl hydrocarbon, the present invention provides an improved process of dehydrating a solvent via azeotropic distillation which uses the said aromatic alkyl hydrocarbon as the azeotropic agent for the separation of acetic acid and methyl acetate from water.

Some aromatic alkyl hydrocarbons form azeotropes with water; for example, either p-xylene or m-xylene forms an azeotrope with approximately 45 wt % (weight %) of water (boiling point: about 93° C.). In contrast, isobutyl acetate employed in the prior art methods gives an azeotropic mixture of 83.5 wt % isobutyl acetate and 16.5 wt % water. Therefore, the aromatic alkyl hydrocarbons are advantageous as an azeotropic agent because of the higher amount of water entrained in the azeotrope, which allows a lower reflux ratio and consequently less energy required for separation of water.

An embodiment of the present invention will be described in detail with reference to the attached FIGURE and a process for producing terephthalic acid, wherein an aromatic carboxylic acid is terephthalic acid and an aromatic alkyl hydrocarbon is p-xylene, also being used as the azeotropic agent. However, the present invention is not construed as being limited thereto.

The major equipment employed in the process of this invention roughly comprises an azeotropic distillation column 6, a decanter 9, and a distillation column 15. The azeotropic distillation column 6 and the distillation column 15 are distillation devices, such as tray columns and packed columns, each of which is equipped with a condenser 3 or 13 at the top of the column and a reboiler 7 or 16 at the bottom of the column. The distillation column 15 is of a conventional type.

In FIG. 1, a feed stream 1 is introduced to the azeotropic distillation column 6, wherein concentrated acetic acid 8, comprising 92 to 99 wt % acetic acid and 1 to 8 wt % water, is withdrawn from the bottom of the column. The top vapor stream 2 of the azeotropic distillation column 6 is condensed and fed to a decanter 9, wherein the condensed liquid is separated into an organic phase (O) and an aqueous phase (A). A small portion of the aqueous-phase liquid 5 and most of the organic-phase liquid 10 are refluxed to the top region of the azeotropic distillation column. A small portion of the organic-phase liquid 11, substantially comprising p-xylene and small amounts of methyl acetate and water, is recycled to the oxidation zone in the manufacturing process of terephthalic acid. A major portion of the aqueous-phase liquid 12, substantially comprising water and small amounts of methyl acetate and acetic acid, is sent to a distillation column 15 for the separation of methyl acetate from water.

The feed stream used in the instant process generally comprises from 30 to 70 wt % acetic acid, 0 to 3 wt % methyl acetate, 0 to 1 wt % p-xylene, and the balance of water, but the feed stream can be a mixture of different compositions. A distillation column with 20 to 70 stages is used as the azeotropic distillation column 6, wherein the temperature at the bottom of the column is preferably maintained within the range of 115 to 145° C. The decanter is preferably operated at a temperature within the range of 20 to 60° C. and at a pressure of from 0.7 to 2.0 kg/cm2 (abs.).

The aqueous-phase liquid 12 from the decanter 9 is supplied to the distillation column 15, wherein methyl acetate is separated from water. Methyl acetate, comprising approximately 80 to 98 wt % methyl acetate, is produced as the top distillate 14 and water, comprising approximately 96 to 99.99 wt % water, is withdrawn from the bottom of the column. A distillation column with 10 to 40 stages is used as the distillation column 15, wherein the temperature at the bottom of the column is preferably maintained within the range of 100 to 120° C.

The foregoing invention provides easier separation of methyl acetate and water and in particular, negligible loss of p-xylene. Since p-xylene is insoluble in water, the loss of p-xylene through the aqueous-phase liquid is negligible. In addition, the separation of methyl acetate from water is much easier than other known processes using azeotropic agents of isobutyl acetate, normal butyl acetate and n-propyl acetate, wherein said azeotropic agents are soluble in the aqueous phase to a certain extent.

In the process of the present invention, the azeotropic agent employed in azeotropic distillation is the same aromatic alkyl hydrocarbon used for the production of the aromatic carboxylic acid; for example, the azeotropic agent is p-xylene for terephthalic acid, m-xylene for isophthalic acid and pseudocumene for trimellitic acid. Therefore, this invention does not introduce a foreign chemical as an azeotropic agent to the process for producing the aromatic carboxylic acid. On the other hand, the prior art methods of azeotropic distillation introduce foreign chemicals as azeotropic agents, such as isobutyl acetate, normal butyl acetate and n-propyl acetate, which contaminate the process for producing the aromatic carboxylic acid. In order to control buildup of p-xylene in the azeotropic distillation process, the prior art methods usually purge a portion of the organic-phase liquid, containing azeotropic agents and p-xylene, to the p-xylene oxidation reactor, wherein the azeotropic agents are decomposed to other impurities such as isobutanol, n-butanol, n-propanol and isopropanol. Such decomposition of azeotropic agents increases consumption of azeotropic agents, while the decomposition products contaminate the process and lower the performance of the azeotropic distillation process.

In the process of this invention for the production of terephthalic acid, the azeotropic agent is p-xylene, the raw material for terephthalic acid, which is oxidized to terephthalic acid when recycled to the p-xylene oxidation reactor, thereby producing no impurities and increasing the yield of terephthalic acid. Furthermore, operating costs for the process of this invention are very low compared to the prior art methods, since the loss of azeotropic agent is negligible and the steam consumption is lower.

Another embodiment of the present invention is described for the case wherein the feed stream substantially contains acetic acid and water. For the separation of acetic acid and water, the process of this invention is practiced without the distillation column (15) and its associated equipment (13, 14, 16, and 17) in FIG. 1. Acetic acid is recovered through the line (8), while water is separated through the line (12). The prior art methods using the azeotropic distillation require another distillation device to recover dissolved azeotropic agents in the aqueous phase. However, this embodiment of the present invention does not require another distillation device, since the azeotropic agent used in this invention is not soluble in the aqueous phase. Therefore, the process of this invention has the advantages of lower investment and operating costs relative to the prior art methods.

The present invention is further illustrated by the following specific examples, which are provided herein for illustration purposes only and are not intended to be limiting.

EXAMPLES

Example 1

A feed stream was fed to an azeotropic distillation column and acetic acid and methyl acetate were substantially separated from water in an apparatus as shown in FIG. 1. Paraxylene was used as the azeotropic agent.

The feed stream, consisting of 55.8 wt % acetic acid, 42.9 wt % water, 1.0 wt % methyl acetate, and 0.3 wt % p-xylene, was continuously fed at a rate of 18.0 kg/hr to the azeotropic distillation column which was a packed column with structured packing, 102 mm in diameter and 4350 mm high. The temperature at the bottom of the column was maintained within the range of 124° C. to 127° C. and the decanter was operated at a temperature of 40° C. and at a pressure of 1.03 kg/cm2 (abs.). The reflux ratio of the azeotropic distillation column was 5.3, while the purge rate of the organic phase was 0.06 kg/hr.

The aqueous-phase liquid comprised 97.62 wt % water, 2.34 wt % methyl acetate, 0.03 wt % p-xylene and 0.01 wt % acetic acid. The organic-phase liquid comprised 90.19 wt % p-xylene, 9.67 wt % methyl acetate, and 0.15 wt % water.

The aqueous-phase liquid from the decanter was continuously pumped at a rate of 7.44 kg/hr to the distillation column 15, which was a packed column with structured packing, 102 mm in diameter and 4450 mm high. The temperature at the bottom of the column was maintained within the range of 105° C. to 108° C. Methyl acetate, comprising 87.1 wt % methyl acetate and 12.9 wt % water, was produced as the top distillate and water, comprising 99.99 wt % water and 0.01 wt % acetic acid, was produced at the bottom of the column.

Example 2

With a feed stream, consisting of 60.0 wt % acetic acid, 38.0 wt % water, 1.95 wt % methyl acetate, and 0.05 wt % p-xylene, the procedure of Example 1 was repeated, except that the reflux ratio of the azeotropic distillation column was changed to 6.4.

The aqueous-phase liquid comprised 94.83 wt % water, 5.13 wt % methyl acetate, 0.03 wt % p-xylene and 0.01 wt % acetic acid. The organic-phase liquid comprised 78.1 wt % p-xylene, 21.58 wt % methyl acetate, and 0.32 wt % water. Methyl acetate, comprising 87.06 wt % methyl acetate and 12.94 wt % water, was produced as the top distillate of the distillation column and water, comprising 99.99 wt % water and 0.01 wt % acetic acid, was produced at the bottom of the column.

Obviously, additional modifications and variations of this invention are possible based on the above teachings. Therefore, it is to be understood that within the scope of the appended claims, this invention may be practiced otherwise than specifically described herein.

What is claimed is:

1. In a process of manufacturing an aromatic carboxylic acid in which an aromatic alkyl hydrocarbon is oxidized with an oxygen-containing gas in acetic acid solution, at a temperature within the range of 150 to 220° C. and at a pressure within the range of 10 to 25 kg/cm (abs.), and in the presence of a catalyst system containing cobalt, manganese and bromine, whereby water and methyl acetate are produced as the by-products of oxidation, and a portion of the condensed liquid from the overhead vapor stream of the oxidation reactor and other dilute acetic acid streams, containing mostly water and methyl acetate, the portion of the condensed liquid and the other dilute acetic acid are collectively called "said feed stream" below, are sent to the dehydration unit where water and methyl acetate are separated from acetic acid, the improvement in the recovery of the acetic acid and the methyl acetate comprises the following steps:

(a) feeding said feed stream containing mostly acetic acid, water and methyl acetate to an azeotropic distillation column in which the azeotropic agent is the same aromatic alkyl hydrocarbon as the feedstock used for the production of the aromatic carboxylic acid;

(b) withdrawing concentrated acetic acid from the bottom of said azeotropic distillation column, condensing the vapor stream of said azeotropic distillation column that is comprised of the azeotropic agent, water and methyl acetate, feeding the liquid condensate to a decanter, separating said condensate into an aqueous phase and an organic phase, refluxing a small portion of the aqueous-phase liquid and a major portion of the organic-phase liquid to the top region of said azeotropic distillation column, withdrawing a major portion of the aqueous-phase liquid comprised predominantly of water and methyl acetate, withdrawing a small portion of the organic-phase liquid comprised predominantly of the azeotropic agent and small amounts of methyl acetate and water;

(c) recycling said concentrated acetic acid and the withdrawn organic-phase liquid to the oxidation reactor section of the aromatic alkyl hydrocarbon, and supplying the withdrawn aqueous-phase liquid to a distillation column in which water and methyl acetate are separated from the bottom and the top of said distillation column, respectively, wherein the azeotropic agent is the very same aromatic alkyl hydrocarbon which is supplied as the reactant for the oxidation reaction, without separately adding any other azeotropic agent in the azeotropic distillation column.

2. The process of claim 1 wherein the aromatic alkyl hydrocarbon is selected from the group consisting of p-xylene, m-xylene, o-xylene, pseudocumene, and mesitylene.

3. The process of claim 1 wherein the decanter is operated at a temperature within the range of 20 to 60° C. and at a pressure within the range of 0.7 to 2.0 kg/cm2 (abs.).

4. The process of claim 1 wherein the product from the bottom of the azeotropic distillation column is substantially free of the azeotropic agent and contains acetic acid preferably within the range of 90% to 99.9% by weight.

5. The process of claim 1 wherein the product from the bottom of the distillation column contains acetic acid within the range of 0.01% to 0.5% by weight.

6. The process of claim 1 wherein the product from the top of the distillation column is substantially free of the azeotropic agent and contains methyl acetate within the range of 80% to 99% by weight.

7. A method for recovering acetic acid from a mixture containing substantially acetic acid and water which comprises distilling said mixture in the presence of an azeotropic agent, recovering acetic acid as the product from the bottom of an azeotropic distillation column, condensing the overhead vapor stream of the azeotropic distillation column, separating the condensate in a decanter into an aqueous phase and an organic phase, refluxing the organic-phase liquid and a portion of the aqueous-phase liquid to said azeotropic distillation column, and withdrawing the aqueous-phase liquid comprised predominantly of water, wherein said azeotropic agent is selected from the group consisting of p-xylene, m-xylene, o-xylene, pseudocumene, and mesitylene.

* * * * *